United States Patent
Cecere et al.

(10) Patent No.: US 9,726,195 B2
(45) Date of Patent: Aug. 8, 2017

(54) AXIAL FLOW BLOOD PUMP

(71) Applicants: Renzo Cecere, Town of Mont Royal (CA); Young Hoon Chung, Montreal (CA); Rosaire Mongrain, Montreal (CA); Toufic Azar, Montreal (CA)

(72) Inventors: Renzo Cecere, Town of Mont Royal (CA); Young Hoon Chung, Montreal (CA); Rosaire Mongrain, Montreal (CA); Toufic Azar, Montreal (CA)

(*) Notice: Subject to any disclaimer, the term of this patent is extended or adjusted under 35 U.S.C. 154(b) by 0 days.

(21) Appl. No.: 15/079,810

(22) Filed: Mar. 24, 2016

(65) Prior Publication Data

US 2016/0279311 A1    Sep. 29, 2016

Related U.S. Application Data

(60) Provisional application No. 62/138,328, filed on Mar. 25, 2015.

(51) Int. Cl.
*A61N 1/362* (2006.01)
*F04D 29/54* (2006.01)
*F04D 3/02* (2006.01)
*F04D 29/18* (2006.01)
*F04D 13/06* (2006.01)
*A61M 1/10* (2006.01)

(52) U.S. Cl.
CPC .......... *F04D 29/548* (2013.01); *A61M 1/101* (2013.01); *F04D 3/02* (2013.01); *F04D 13/0606* (2013.01); *F04D 13/0646* (2013.01); *F04D 29/181* (2013.01)

(58) Field of Classification Search
CPC ...... A61M 1/1025; F04D 3/02; F04D 29/181; F04D 29/168; F04D 29/548; F04D 13/02; F04D 29/528; F04D 29/242
See application file for complete search history.

(56) References Cited

U.S. PATENT DOCUMENTS

| | | | |
|---|---|---|---|
| 2012/0134832 A1* | 5/2012 | Wu | A61M 1/101 416/198 R |
| 2013/0209292 A1 | 8/2013 | Baykut et al. | |
| 2016/0089482 A1* | 3/2016 | Siegenthaler | A61F 2/24 600/16 |

* cited by examiner

*Primary Examiner* — Robert N Wieland (57) ABSTRACT

An axial flow blood pump having a rotor rotatably mounted in a housing. The rotor includes at least two rotor blades having different configurations.

24 Claims, 6 Drawing Sheets

AXIAL FLOW BLOOD PUMP

FIELD OF THE INVENTION

The present invention relates to the art of medical devices. More specifically, the present invention is concerned with an axial flow blood pump.

BACKGROUND

Many cardiac pathologies require a heart transplant. However, there are more patients than heart donors available and there is often a need to use a mechanical device to assist the patient's heart while waiting for a suitable donor. For example, blood pumps are used to assist the heart in patient with severe congestive heart failure. One problem associated with such pumps is that they often create large shear forces in the blood, which can cause blood cell degradation over time, such as hemolysis. Such degradation is toxic to the patient. Another problem is that the design of most blood pumps are tuned to function optimally in a short range of RPM (rotations per minutes) thus rendering them less efficient along all patient regimes and therefore creating potentially more turbulence, shear stress and cavitation, which cause again blood cell degradation. As blood flow in humans varies naturally significantly when the patient switches between resting and moving, such pumps design induce inefficiencies affecting adversely blood degradation.

Accordingly, there is a need in the industry to provide an improved blood pump. An object of the present invention is therefore to provide such an improved blood pump.

SUMMARY OF THE INVENTION

In a broad aspect, the invention provides an axial flow blood pump, comprising: a hollow housing defining a housing inlet, a housing outlet and a housing axial axis extending therebetween; a rotor mounted in the housing so as to be rotatable about the housing axial axis, the rotor including at least two rotor blades, a first rotor blade from the at least two rotor blades having a first configuration and a second rotor blade from the at least two rotor blades having a second configuration; and an actuator operatively coupled to the housing and to the rotor to selectively rotate the rotor in the housing about the housing axial axis; wherein the first and second configurations differ from each other.

Advantageously, the use of rotor blades having two or more configurations within a single rotor allows the rotor to accommodate optimally many flow regimes through the pump.

The invention may also provide an axial flow blood pump wherein the first and second rotor blades are coiled around the housing axial axis, the first rotor blade defining first blade inlet and outlet ends respectively receiving and releasing blood when the rotor is operated in a patient and the second rotor blade defining second blade inlet and outlet ends respectively receiving and releasing blood when the rotor is operated in a patient.

The invention may also provide an axial flow blood pump wherein the first and second rotor blades each extend along a respective ruled surface.

The invention may also provide an axial flow blood pump wherein the first and second configurations differ in pitch relative to the housing axial axis.

The invention may also provide an axial flow blood pump wherein the pitch of the first blade is constant at all axial positions along the first blade.

The invention may also provide an axial flow blood pump wherein the rotor is a hollow rotor including a rotor body at the periphery thereof delimiting a rotor passageway extending axially therealong, the rotor body defining a body internal surface delimiting the rotor passageway, the first and second blades extending from the body internal surface circumferentially spaced apart from each other.

The invention may also provide an axial flow blood pump wherein a third rotor blade from the at least two rotor blades has the first configuration and a fourth rotor blade from the at least two rotor blades has a second configuration, the third and fourth blades extending from the body internal surface.

The invention may also provide an axial flow blood pump wherein the second rotor blade is provided circumferentially between the first and third rotor blades.

The invention may also provide an axial flow blood pump wherein the first rotor blade defines a blade height at each given axial position therealong as a distance between the body internal surface and the radially inwardmost location of the first rotor blade at the given axial position, the first rotor blade having a substantially constant height axially therealong.

The invention may also provide an axial flow blood pump wherein the first and second rotor blades have different heights.

The invention may also provide an axial flow blood pump wherein the first rotor blade defines a blade height at each given axial position therealong as a distance between the body internal surface and the radially inwardmost location of the first rotor blade at the given axial position, the first rotor blade having a larger height at the first blade inlet end than at the first blade outlet end.

The invention may also provide an axial flow blood pump wherein the first rotor blade defines a blade height at each given axial position therealong as a distance between the body internal surface and the radially inwardmost location of the first rotor blade at the given axial position, the first rotor blade having a larger height at the first blade outlet end than at the first blade inlet end.

The invention may also provide an axial flow blood pump wherein the rotor defines an axially extending lumen unobstructed by the rotor blades, the lumen having a substantially constant transversal cross-sectional configuration axially therealong.

The invention may also provide an axial flow blood pump wherein the rotor defines an axially extending lumen unobstructed by the rotor blades, the lumen tapering in one of a direction leading from the first blade inlet end towards the first blade outlet end and a direction leading from the first blade outlet end towards the first blade inlet end.

The invention may also provide an axial flow blood pump wherein the first rotor blade increases in thickness in a direction leading from the first blade inlet end towards the first blade outlet end along at least part of the first rotor blade.

The invention may also provide an axial flow blood pump wherein the first rotor blade decreases in thickness in a direction leading from the first blade inlet end towards the first blade outlet end along at least part of the first rotor blade.

The invention may also provide an axial flow blood pump wherein the first rotor blade defines a first rotor blade inlet portion, a first rotor blade outlet portion and a gap therebetween.

The invention may also provide an axial flow blood pump wherein the rotor includes a rotor body at the periphery thereof delimiting a rotor passageway extending axially therealong, and an internal shroud extending axially in the rotor passageway, the rotor body defining a body internal surface, the internal shroud defining a shroud external surface facing the body internal surface and a shroud internal surface, the first rotor blade extending between the body internal surface and shroud external surface and the second rotor blade extending from the shroud internal surface.

The invention may also provide an axial flow blood pump further comprising at least one of a flow inducer provided upstream of the housing inlet and including at least one vane which is shaped to redirect a blood flow entering the rotor to create a vortex; and a diffuser provided downstream of the housing outlet and shaped for at least partial straightening of a blood flow exiting the rotor.

The invention may also provide an axial flow blood pump wherein the first rotor blade is chamfered at the first blade inlet end.

The invention may also provide an axial flow blood pump wherein the housing and rotor both have a substantially cylindrical configuration.

The invention may also provide an axial flow blood pump wherein the rotor defines axially opposed rotor inlet and outlet, the rotor tapering in a direction selected from a direction leading from the rotor inlet to the rotor outlet and a direction leading from the rotor outlet to the rotor inlet.

The invention may also provide an axial flow blood pump wherein the rotor has a substantially frusto-conical configuration.

The invention may also provide an axial flow blood pump wherein the first rotor blade extends circumferentially around the rotor over less than one full turn.

The invention may also provide an axial flow blood pump wherein the first rotor blade extends circumferentially around the rotor over one of less than half a full turn and less than a quarter of a full turn.

In another broad aspect, the invention provides an axial flow blood pump, comprising: a hollow housing defining a housing inlet, a housing outlet and a housing axial axis extending therebetween; a hollow rotor mounted in the housing so as to be rotatable about the housing axial axis, the hollow rotor defining a rotor body and a rotor passageway extending axially therealong, the rotor including at least one rotor blade, the at least one rotor blade being coiled around the housing axial axis, the at least one rotor blade extending at most one full turn around the housing axial axis; and an actuator operatively coupled to the housing and to the rotor to selectively rotate the rotor in the housing about the housing axial axis. The invention may also provide such an axial flow blood pump that has configurations including one or more of the various characteristics mentioned hereinabove.

Other objects, advantages and features of the present invention will become more apparent upon reading of the following non-restrictive description of preferred embodiments thereof, given by way of example only and in relation with the following Figures.

BRIEF DESCRIPTION OF THE DRAWINGS

FIG. 1, in a perspective view, illustrates a blood pump in accordance with an embodiment of the present invention;

FIG. 2, in a perspective exploded view with hidden lines not shown, illustrates the blood pump of FIG. 1;

FIG. 3, in a perspective exploded view with hidden lines shown, illustrates the blood pump of FIGS. 1 and 2;

FIG. 4, in a side cross-sectional view along section line IV-IV of FIG. 5, illustrates the blood pump of FIGS. 1 to 3;

FIG. 5, in a front plan view, illustrates the blood pump of FIGS. 1 to 4;

FIG. 6, in a perspective view, illustrates an alternative rotor usable in the blood pump shown in FIGS. 1 to 5;

FIG. 7, in a front elevation view illustrates the rotor of FIG. 6;

FIG. 8, in a front elevation view, illustrates another alternative rotor usable in the blood pump shown in FIGS. 1 to 5;

FIG. 10, in a perspective view without hidden lines shown, illustrates yet another alternative rotor usable in the blood pump shown in FIGS. 1 to 5;

FIG. 11, in a perspective view with hidden lines shown, illustrates the rotor shown in FIG. 10;

FIG. 12, in a front plan view, illustrates the rotor of FIGS. 10 and 11;

FIG. 13, in a front plan view, illustrates yet another alternative rotor usable in the blood pump shown in FIGS. 1 to 5;

FIG. 14, in a side cross-sectional view taken along section line XIV-XIV of FIG. 13, illustrates the rotor shown in FIG. 13;

FIG. 15, in a front plan view, illustrates yet another alternative rotor usable in the blood pump shown in FIGS. 1 to 5;

FIG. 16, in a side cross-sectional view taken along section line XVI-XVI of FIG. 15, illustrates the rotor shown in FIG. 15;

DETAILED DESCRIPTION

The term "substantially" is used throughout this document to indicate variations in the thus qualified terms. These variations are variations that do not materially affect the manner in which the invention works and can be due, for example, to uncertainty in manufacturing processes or to small deviations from a nominal value or ideal shape that do not cause significant changes to the invention. These variations are to be interpreted from the point of view of the person skilled in the art. The present application claims priority from provisional patent application Ser. No. 62/138,328 filed Mar. 25, 2015, the contents of which is hereby incorporated by reference in its entirety.

Figures 1, 2:
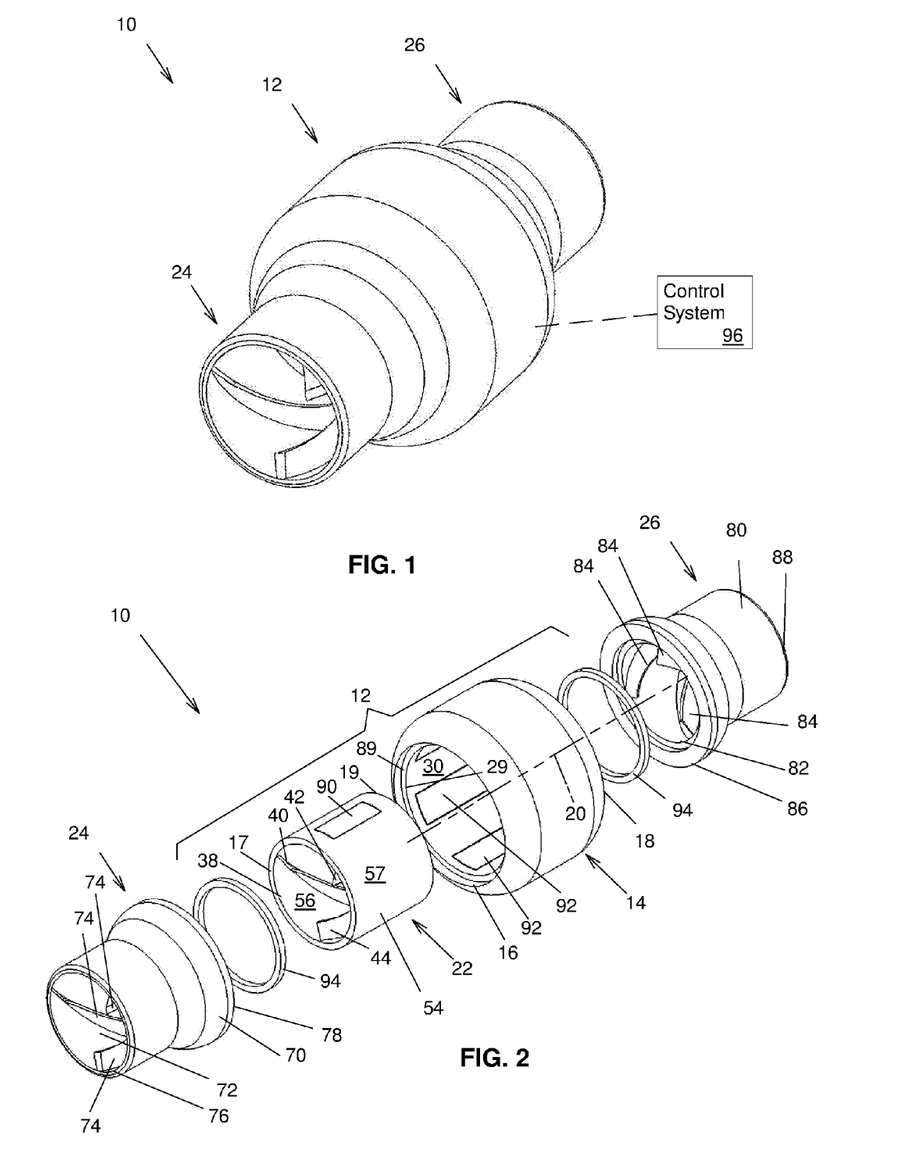

Referring to FIG. 1, there is shown an axial flow blood pump 10 in accordance with an embodiment of the invention, referred to simply as pump 10 hereinbelow. The pump 10 is usable, for example, to assist the heart of heart failure patients in a conventional manner. The pump 10 is controlled by a control system 96. The link between the control system 96 and the pump 10 is shown in dashed line as it may be a wireless link, a wired link, an optical link, a sound wave link, or any combinations thereof. The control system 96 provides power to the pump 10 and controls the application of this power to achieve a desired flow rate of blood through the pump 10. Typically, power is provided through a wire, but rechargeable battery-powered pumps 10, or otherwise powered pumps 10, are within the scope of the invention.

Figure 3:
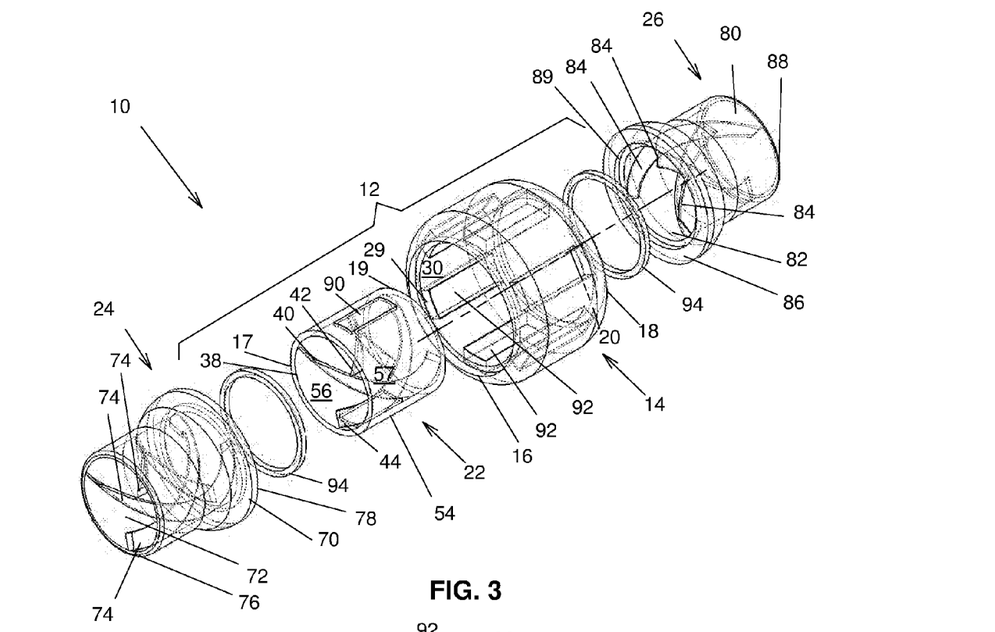

As better seen in FIGS. 2 and 3, the pump 10 includes a pump section 12 including a hollow housing 14 defining a housing inlet 16, a housing outlet 18 and a housing axial axis 20 extending therebetween. The pump section 12 also includes a rotor 22 mounted in the housing 14 so as to be rotatable about the housing axial axis 20 and an actuator 28 (identified in FIG. 4) operatively coupled to the housing 14 and to the rotor 22 to selectively rotate the rotor 22 in the housing 14 about the housing axial axis 20. Typically, the pump 10 also includes a flow inducer 24 provided upstream of the housing inlet 16 and a diffuser 26 provided downstream of the housing outlet 18. However, in alternative embodiments, the flow inducer 24, the diffuser 26 or both of them are omitted.

Figure 4:
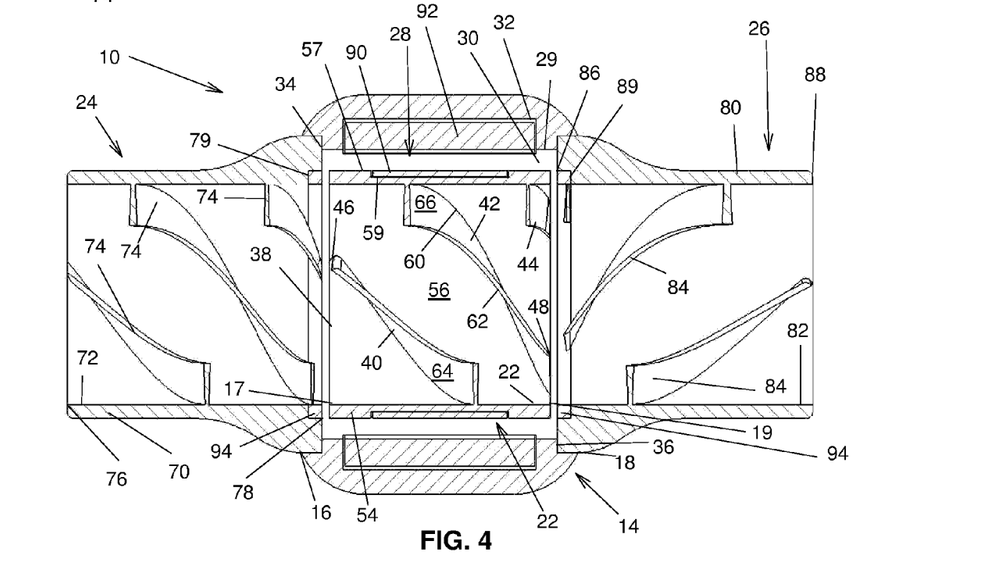

The housing 14 is generally cylindrical and tubular in configuration, but other configurations are within the scope of the invention. Referring to FIG. 4, the housing 14 defines a housing passageway 29 extending axially therealong delimited by a housing internal surface 30. Recesses 32 are formed in the housing 14, extending for example from the housing internal surface 30. The recesses 32 are for example elongated and axially aligned. Typically, many recesses 32 are provided circumferentially spaced apart from each other. The recesses 32 are provided for receiving thereinto parts of the actuator 28. In some embodiments, the housing 14 defines annular ledges 34 and 36 substantially adjacent the housing inlet and outlet 16 and 18 respectively. In these embodiments, the housing passageway 29 has a slightly larger diameter at the housing inlet and outlet 16 and 18 than along most of its length.

The rotor 22 defines rotor inlet and outlet 17 and 19 provided respectively substantially adjacent the housing inlet and outlet 16 and 18. The rotor 22 includes at least one rotor blade 40. In some embodiments, the rotor 22 includes at least two rotor blades 40 and 42. In the rotor 22 shown in FIGS. 1 to 5, the rotor 22 includes another rotor blade 44, for a total of three rotor blades 40, 42 and 44. However, any other suitable number of rotor blades 40, 42 and 44 is within the scope of the invention. Each rotor blade 40, 42 and 44 defines axially opposed blade inlet and outlet ends 46 and 48, typically substantially adjacent to the housing inlet and outlet 16 and 18 respectively. The blade inlet and outlet ends 46 and 48 respectively receive and release blood when the rotor 22 is operated in a patient, the blood being moved along the rotor blades 40, 42 and 44 between the blade inlet and outlet ends 46 and 48 when the rotor 22 is rotated.

The rotor 22 defines a rotor passageway 38 extending axially therealong between the rotor inlet and outlet 17 and 19. Thus, the rotor 22 is a hollow rotor 22, also called a coreless rotor 22, and the rotor blades 40, 42 and 44 are provided in the rotor passageway 38. However, in some embodiments (not shown in the drawings), the rotor 22 is of a type including a central hub from which the rotor blades 40, 42 and 44 extend outwardly.

In some embodiments, the rotor blades 40, 42 and 44 all have the same configuration. In this document, rotor blades 40, 42 and 44 have the same configuration if it is possible to superpose the shapes of the surfaces defining the rotor blades 40, 42 and 44 by rotating and translating these shapes in space, without any deformation. In other embodiments, such as in rotor 22a shown in FIGS. 6 to 9 and further described hereinbelow, the rotor blades do not have all the same configuration. The configurations may differ in one or more parameters, such as in one or more of pitch, height and thickness, among other possibilities. These terms are further defined hereinbelow.

The rotor 22 is a coreless rotor in which the rotor blades 40, 42 and 44 do not extend from a central hub, but from the periphery of the rotor 22. More specifically, the rotor 22 includes a rotor body 54 at the periphery thereof delimiting the rotor passageway 38. The rotor body 54 defines a body internal surface 56 and an opposed body external surface 57. The rotor blades 40, 42 and 44 extend from the body internal surface 56. Recesses 59 are formed in the body external surface 57.

For example each of the rotor blades 40, 42 and 44 extends along substantially the entire axial length of the rotor body 54 and the rotor blades 40, 42 and 44 are circumferentially spaced apart from each other. However, in alternative embodiments, the rotor blades 40, 42 and 44 extend along only part of the axial length of the rotor body 54. Thus, the rotor blades 40, 42 and 44 are coiled around the housing axial axis 20. That is the intersection of the rotor blades 40, 42 and 44 with the rotor body 54 forms a curve that jointly turns around and advances along the housing axial axis 20, in the manner of a coil.

Also, in other embodiments (not shown in the drawings), one or more of the rotor blades 40, 42 and 44 extend outwardly from the body external surface 57 of the rotor body 54. In yet other embodiments, as described in further details hereinbelow, the rotor 22 is replaced by a double shrouded rotor 22k. In yet other embodiments (not shown in the drawings), the rotor 22 is replaced by a rotor including a conventional hub from which rotor blades extend outwardly.

In the following description of the rotor blades 40, 42 and 44 and of their variants, the following terminology is used. The rotor blades 40, 42 and 44 have a generally helicoidal configuration along the rotor body 54. Each rotor blade 40, 42 and 44 has a base 60, where the rotor blade 40, 42 and 44 contacts the surface from which it extends, for example the body internal surface 56, and a free edge 62 opposed to the base 60. In the rotor blades 40, 42 and 44, the free edge 62 is the line formed by the union of all the radially inwardmost locations of the rotor blades 40, 42 and 44 at all axial positions therealong. However, in other embodiments, the free edge 62 is not at the radially inwardmost position.

The height of the rotor blades 40, 42 and 44 is defined as the distance between the free edge 62 and the surface from which the base 60 extends. In embodiments in which the rotor blades 40, 42 and 44 are perpendicular to this surface, the height is the distance between the base 60 and the free edge 62 along a line perpendicular to the surface from which the base 60 extends.

The rotor blades 40, 42 and 44 each define an inlet facing surface 64 and an opposed outlet facing surface 66, facing respectively the rotor inlet and outlet 17 and 19. The thickness of the rotor blades 40, 42 and 44 is defined as the distance between the inlet and outlet facing surfaces 64 and 66. This distance is taken along lines perpendicular to the inlet and outlet facing surfaces 64 and 66 when the latter are parallel to each other, and along a line perpendicular to a surface bisecting the inlet and outlet facing surfaces 64 and 66 when the latter are not parallel to each other.

The pitch of the rotor blades 40, 42 and 44 is defined as the axial distance required to complete one complete circumference of the rotor 22. This distance may be in absolute terms, such a in inches or centimeters, or relative to the radius of the rotor 22. This definition is valid when the pitch is constant along the whole rotor blade 40, 42 and 44, as is the case in the rotor 22. In cases in which the rotor blade 40, 42 and 44 varies in pitch axially therealong, which is within the scope of the invention but not shown in the drawings, the pitch can be defined as the derivative of the distance from the housing inlet 16 relative to an angle around the rotor 22 multiplied by a constant that depends from the units of angle. If the angles are measured in radians, the constant is 2×pi. The pitch angle is the angle made by the base 60 with an axis parallel to the housing axial axis 20 intersecting the base 60.

The rotor blades 40, 42 and 44 each extend along a respective ruled surface, but other configurations are within the scope of the invention. A ruled surface is defined as a surface that can be formed by moving a straight segment in space. The rotor blades 40, 42 and 44 have a same constant pitch at all axial positions therealong. Also the rotor blades 40, 42 and 44 have a similar constant thickness along their whole axial length and their whole height. Finally, the rotor blades 40, 42 and 44 have a substantially constant height axially therealong and this height is the same for all the rotor blades 40, 42 and 44. However, in other embodiments, one or more of the rotor blades 40, 42 and 44 may have a pitch, a thickness or a height that varies at different locations therealong, as described in further details hereinbelow.

Typically, the rotor 22 defines an axially extending lumen 68 (identified in FIG. 5) unobstructed by the rotor blades 40, 42 and 44. In other words, there is a volume in the rotor passageway 38 through which axial flow of blood is not interrupted by any surface. The lumen 68 has a substantially constant transversal cross-sectional configuration therealong, and more specifically, the lumen 68 has a substantially cylindrical configuration in the rotor 22, but other configurations are within the scope of the invention. In this document, the difference between a passageway and a lumen is that objects may be provided in a passageway. For examples, the rotor blades 40, 42 and 44 are in a passageway, the rotor passageway 38. However, a lumen, such as the lumen 68, is a free space through which a fluid can flow uninterrupted.

In some embodiments, at least one of the rotor blades 40, 42 and 44, for example the first rotor blade 40, extends circumferentially over less than one full turn. In other words, in such embodiments, there exists a line parallel to the housing axial axis 20 located on the body internal surface 56 that does not intersect the at least one of the blades 40, 42 and 44, and more specifically its base 60. Typically, but not exclusively, in such embodiments all the rotor blades 40, 42 and 44 extend circumferentially around the rotor 22 over less than one full turn. In other embodiments, the first rotor blade 40 extends circumferentially around the rotor 22 over less than half a full turn. In yet other embodiments, the first rotor blade 40 extends circumferentially around the rotor over less than a quarter of a full turn. Such rotor blades that do not extend over one full turn are advantageous in providing more head pressure at the rotor outlet 19, when compared to rotor blades that do extend over more than one full turn. However, in other embodiments, one or more of the rotor blades 40, 42 and 44 extends over at least one full turn around the housing axial axis 20. In some of the embodiments described in the present paragraph, the rotor blades 40, 42 and 44 may have all the same configuration. In other of these embodiments, the rotor blades 40, 42 and 44 may have different configurations and their number may be any suitable number of rotor blades.

Referring to FIGS. 2 and 3, the flow inducer 24 is of a conventional type including an inducer housing 70 defining an inducer passageway 72 in fluid communication with the housing passageway 29. The inducer housing 70 defines inducer housing inlets and outlets 76 and 78. A relatively small portion of the inducer housing 70 is partially inserted in the housing 14 at the housing inlet 16 and abuts against the ledge 34. The flow inducer 24 defines an inducer recess 79 (better seen in FIG. 4) at the inducer housing outlet 78. The inducer recess 79 has for example a substantially annular configuration provided radially outwardly of the inducer passageway 72 and opens towards the housing 14. The inducer recess 79 receives components of the actuator 28, as described hereinbelow.

One or more inducer blades 74 are provided in the inducer passageway 72. The inducer blades 74 have configurations similar to any of the rotor blades described herein, and may even have different configurations within the same flow inducer 24, similarly to the rotor blades. However, the inducer blades 74 are static relative to the inducer housing 70, and thus static relative to the housing 14. The inducer blades 74 are configured to guide the incoming blood flow towards the leading edge of the rotor blades 40, 42 and 44 and induce a smoother flow transition.

While a specific flow inducer 24 is described herein, any other conventional suitable flow inducer may be used in the pump 10.

Returning to FIGS. 2 and 3, the diffuser 26 is of a conventional type including a diffuser housing 80 defining a diffuser passageway 82 in fluid communication with the housing passageway 29. The diffuser housing 80 defines diffuser housing inlets and outlets 86 and 88. A relatively small portion of the diffuser housing 80 is partially inserted in the housing 14 at the housing outlet 18 and abuts against the ledge 36. The diffuser 26 defines a diffuser recess 89 at the diffuser housing inlet 86. The diffuser recess 89 has for example a substantially annular configuration provided radially outwardly of the diffuser passageway 82 and opens towards the housing 14. The diffuser recess 89 receives component of the actuator 28, as described hereinbelow.

One or more diffuser blades 84, which are also referred to as vanes in the art, are provided in the diffuser passageway 82. The diffuser blades 84 have configurations similar to any of the rotor blades described herein, and may even have different configurations within the same diffuser 26, similarly to the rotor blades. However, the diffuser blades 84 are static relative to the diffuser housing 80, and thus static relative to the housing 14. The diffuser blades 84 are configured to accept the blood incoming at the diffuser 26, which moves in a vortex, and to at least partially straighten the flow of blood as it exits the diffuser 26.

While a specific diffuser 26 is described herein, any other conventional suitable diffuser may be used in the pump 10.

The actuator 28, referred to in FIG. 4, has two functions. First, the actuator 28 acts as a magnetic bearing to suspend the rotor 22 in the housing 14. While mechanical bearings could be used in alternative embodiments, magnetic bearings are often advantageous in blood pumps 10. The actuator 28 also rotates the rotor 22 in the housing 14. In a specific embodiment, the actuator 28 is a system including rotor magnetic elements 90, radial static magnetic elements 92 and axial static magnetic elements 94. The actuator 28 is operatively coupled to the control system 96 to be controlled and powered thereby. Such actuators 28 are conventional and the actuator 28 is thus not described in great details.

A non-limiting embodiment of the actuator 28 may be as follows. The rotor magnetic elements 90 are each provided in one of the recesses 59 of the rotor 22. For example, the rotor magnetic elements 90 include permanent magnets. The radial static magnetic elements 92 for example include electromagnets connected to the control system 96 and are provided in the recesses 32. In some embodiments, but not necessarily, the numbers of rotor magnetic elements 90 and radial static magnetic elements 92 are the same. The rotor magnetic elements 90 and radial static magnetic elements 92 are used together to suspend radially the rotor 22 and to rotate the rotor 22. Two axial static magnetic elements 94 are provided, one in the inducer recess 79 and one in the diffuser recess 89. The axial static magnetic elements 94 have a substantially annular configuration and are used to stabilize the axial position of the rotor 22 in the housing 14 through interaction with the rotor magnetic elements 90.

While recesses 32, 59, 79 and 89 have been shown and described to receive the rotor magnetic elements 90, radial static magnetic elements 92 and axial static magnetic elements 94, these latter components could also be embedded in the material forming the flow inducer 24, housing 14, rotor 22 and diffuser 26.

The control system 96 (shown in FIG. 1 only) is conventional and includes the required components to activate the active components of the actuator 28, namely the radial and axial static magnetic elements 92 and 94, to suspend magnetically the rotor 22 in the housing 14 and to rotate the former in the latter. The control system 96 may also include any required sensors to control the rotation speed of the rotor 22, as well as any components that the person skilled in the art would be using in such control systems 96.

In use, the pump 10 is inserted at a suitable location in the circulatory system of a patient. The control system 96 controls operation of the actuator 28 so that the rotor 22 can pump blood through the pump 10 to assist or replace the heart of the patient.

As mentioned at numerous occasions hereinabove, there are many variants to the rotor 22 and rotor blades 40, 42 and 44 that are within the scope of the invention. While many characteristics that may be varied in the rotor 22 and rotor blades 40, 42 and 44 are described hereinbelow, the person skilled in the art will understand that these variants could be combined together. For example, and non-limitingly, rotor blades with non-constant height and rotor blades with non-constant thickness are described. However, a rotor blade with combined non-constant height and non-constant thickness is also within the scope of the invention. All other suitable combinations of characteristics of the variants described below are also within the scope of the invention.

Figures 5, 6, 7, 8:
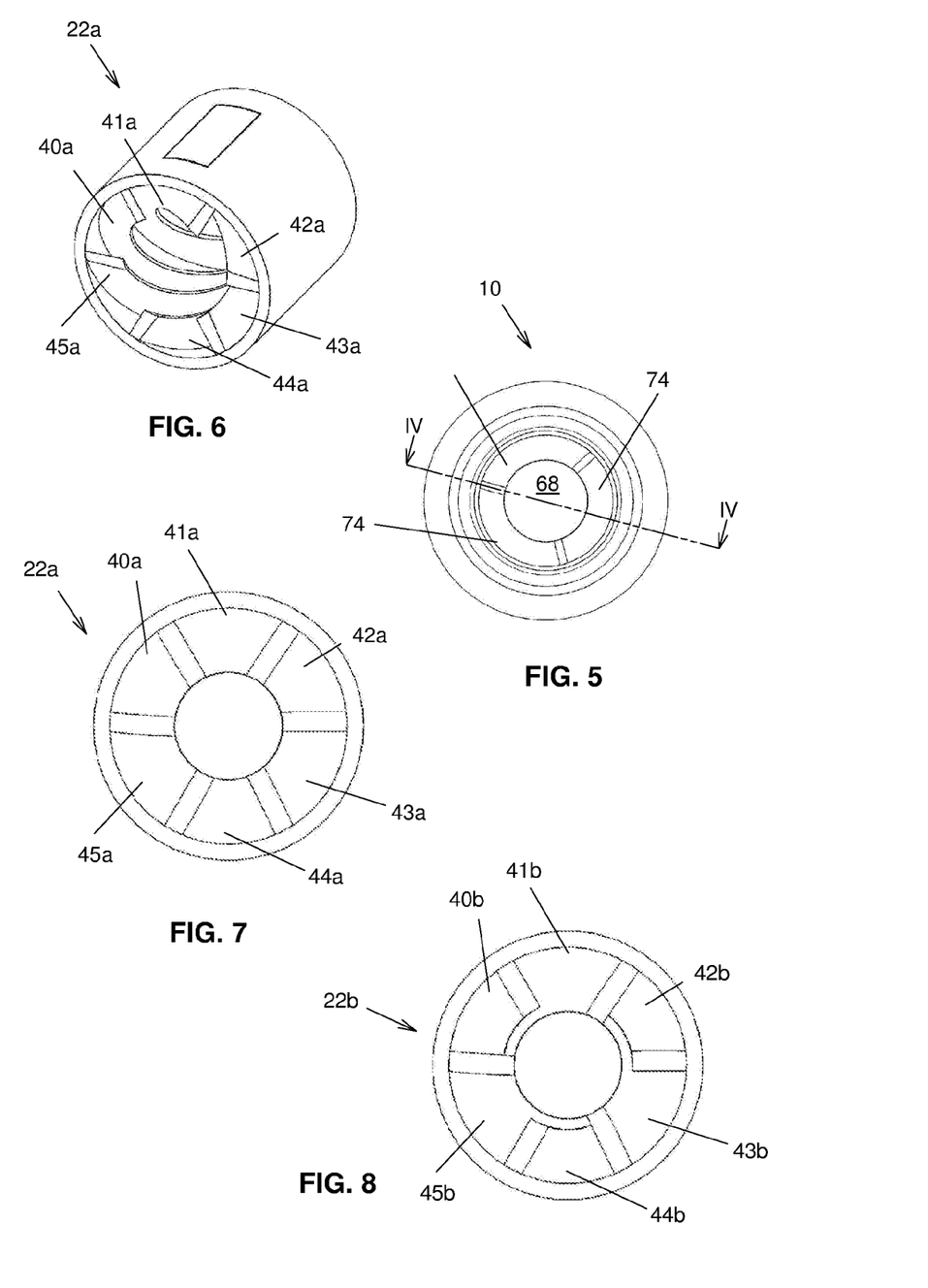

FIGS. 6 and 7 illustrate a rotor 22a with rotor blades that have different configurations. More specifically, the rotor 22a includes rotor blades 40a, 42a and 44a. The rotor blades 40a, 42a and 44a all have the same configuration. However, the rotor 22a also includes rotor blades 41a, 43a and 45a. One of the rotor blades 40a to 45a, for example rotor blade 40a has a first configuration and another one of the rotor blades 40a to 45a, for example rotor blade 41a has a second configuration. The first and second configurations differ from each other. In other words, the geometrical shapes defining the rotor blades 40a and 41a cannot be superposed in space simply through rotation and translation of these shapes. In the present embodiment, the rotor blades 40a, 42a and 44a have a first pitch, and the rotor blades 41a, 43a and 45a have a second pitch that differs from the first pitch. This pitch is constant along each of the blades 40a to 45a. In such embodiments, the total number of rotor blades may be two, three, or more, and is not limited to six rotor blades 40a to 45a as in the rotor 22a. Also, the number of different configurations for the rotor blades 40a to 45a may be larger than 2.

In the rotor 22a, the rotor blades 40a to 45a having different configurations alternate circumferentially around the circumference of the rotor 22a. In other words, there is a rotor blade 40a, 42a or 44a having the first configuration between each pair of the rotor blades 41a, 43a and 45a having the second configuration. However, in other embodiments, the rotor blades 40a to 45a do not necessarily alternate circumferentially. For example, the rotor blades 40a, 42a and 44a having a first configuration could all be adjacent to each other, and the rotor blades 41a, 43a and 45a having the second configuration could also all be adjacent to each other.

The different configurations of the rotor blades 40a to 45a are caused by variations in pitch relative to the housing axial axis 20 (not shown in FIGS. 6 and 7) between the rotor blades 40a to 45a. Surprisingly, it was found that these differences in pitch do not necessarily cause excessive shear stress or cavitation when the rotation speed of the rotor 22a is varied between speeds corresponding to optimal match to one of the pitches.

The rotor blades may differ in other characteristics. For example FIG. 8 illustrates a rotor 22b in which the rotor blades 40b to 45b all have the same pitch. However, the rotor blades 40b, 42b and 44b have a first height, which is constant along each of the rotor blades 40b, 42b and 44b. Also, the rotor blades 41b, 43b and 45b have a second height, which is constant along each of the rotor blades 41b, 43b and 45b, and which is larger than the first height. Here again, the rotor blades 40b to 45b have configurations (ie heights) that alternate along the circumference of the rotor 22b, but other configurations are within the scope of the invention.

Figure 9:
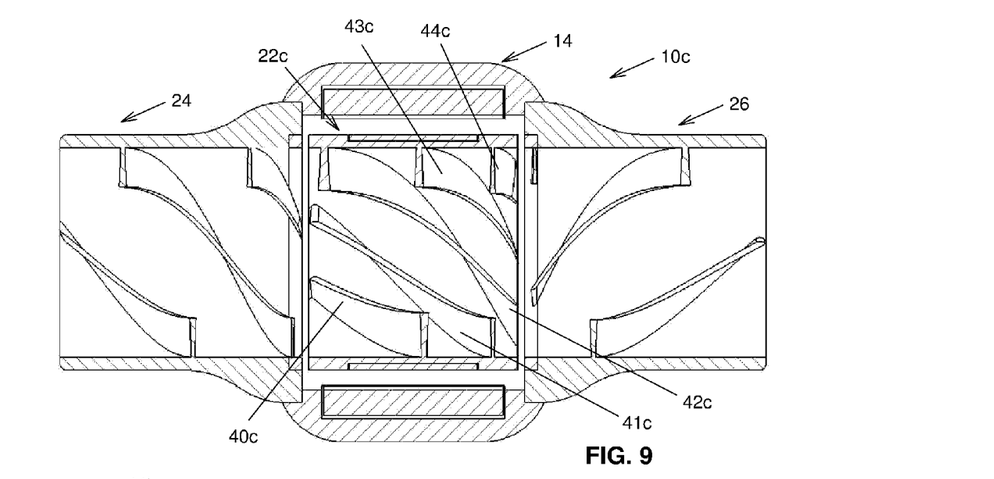
FIG. 9, in a side cross-sectional view, illustrates an alternative blood pump including yet another alternative rotor.

FIG. 9 illustrates a pump 10c in which the rotor 22c has rotor blades 40c, 41c, 42c, 43c, 44c, along with a sixth rotor blade that is not visible in FIG. 9. Different ones of the rotor blades 40c to 44c differ in both pitch and height.

Figures 13, 14, 15, 16:
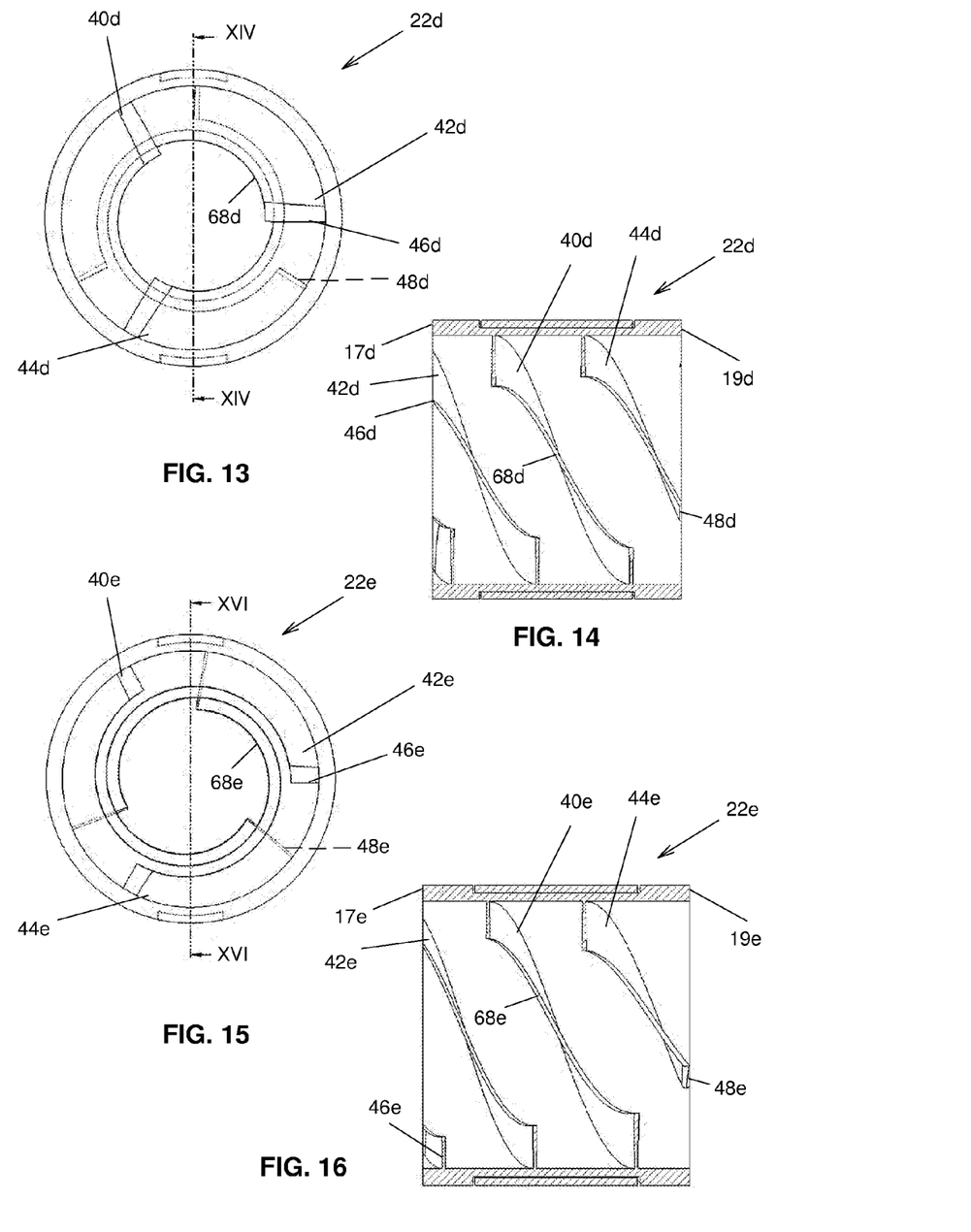

In yet other embodiments, as seen in the rotor 22d of FIGS. 13 and 14, the rotor blades 40d, 42d and 44d all have similar configurations, but the height of each of the blades 40d, 42d and 44d varies axially therealong. More specifically, rotor blades 40d, 42d and 44d have a larger height at the blade inlet end 46d than at the blade outlet end 48d. This creates a lumen 68d that tapers in a direction leading from the blade outlet end 48d towards the blade inlet end 46d. Variations in heights such as those recited above influence boundary flow along the rotor blades 40d, 42d and 44d that would directly influence the suction effect created on the blood going inside the lumen 68d. They also allow control over velocity and pressure gradient of blood flow in the pump 10.

FIGS. 15 and 16 illustrate a similar variation in a rotor 22e, with the exception that the height variation is reversed, with rotor blades 40e, 42e and 44e have a larger height at the blade inlet end 46e than at the blade outlet end 48e. This creates a lumen 68e that tapers in a direction leading from the blade inlet end 46d towards the blade outlet end 48d.

Figures 17, 18:
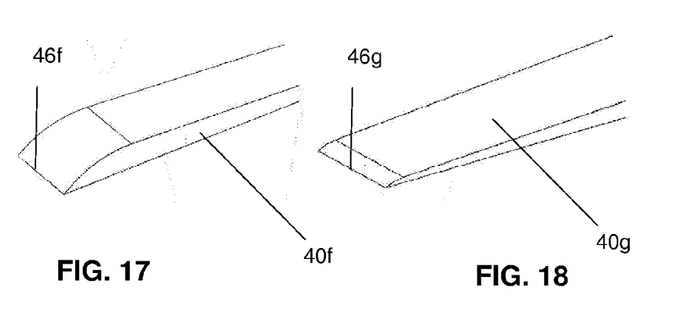
FIG. 17, in a perspective developed view, illustrates an alternative rotor blade usable in the rotors and blood pumps of FIGS. 1 to 16.
FIG. 18, in a perspective developed view, illustrates another alternative rotor blade usable in the rotors and blood pumps of FIGS. 1 to 16.

FIG. 17 illustrates a rotor blade 40f that increases in thickness in a direction leading away from the blade inlet end 46f along at least part of the rotor blade 40f. The rotor blade 40f is shown developed to clearly illustrate the variations in thickness, as if the rotor to which it attaches had been cut longitudinally and flattened. More specifically, the rotor blade 40f is chamfered at the blade inlet end 46f, along a relatively small portion thereof, so that the blood flow is gradually separated by the blade 46f as the latter rotates. However, after termination of the chamfered portion, the rotor blade 40f tapers gradually in thickness away from the blade inlet end 46f.

FIG. 18 illustrates, also developed, the situation opposite to that of FIG. 17, with a rotor blade 40g that increases in thickness in a direction leading away from the blade inlet end 46g along at least part of the rotor blade 40g. More specifically, the rotor blade 40g is chamfered at the blade inlet end 46g, along a relatively small portion thereof. After termination of the chamfered portion, the rotor blade 40g increases gradually in thickness in a direction leading away from the blade inlet end 46g.

Other variations in thickness are also within the scope of the invention. For example, a rotor blade (not shown in the drawings) could have a portion of constant thickness adjacent to a decreasing or increasing thickness portion. Also, rotor blades of constant or varying thickness could be mixed with each other in a single rotor.

Figure 19:
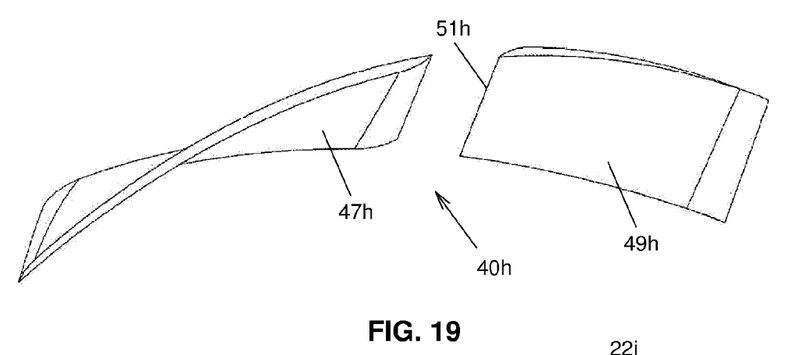
FIG. 19, in a perspective view, illustrates yet another alternative rotor blade usable in the rotors and blood pumps of FIGS. 1 to 16.

FIG. 19 illustrates a discontinuous rotor blade 40h. More specifically, the rotor blade 40h defines a rotor blade inlet portion 47h, a rotor blade outlet portion 49h and a gap 51h therebetween. Of course the gap 51h could be present or absent in different blades within a given rotor, and the gap 51h could be provided in any other suitable blade described herein, and thus combined with variations in height, pitch, and thickness.

Figure 20:
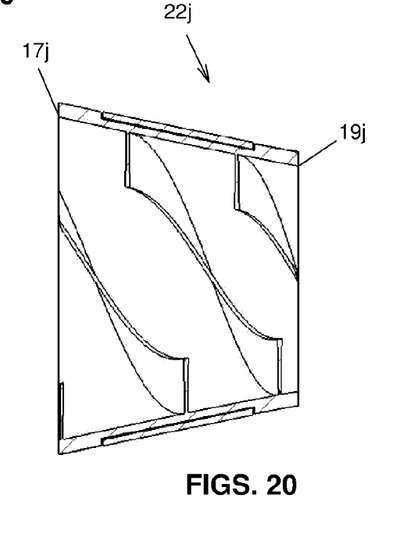
FIG. 20, in a side cross-sectional view, illustrates yet another alternative rotor usable in another alternative blood pump.
Figure 21:
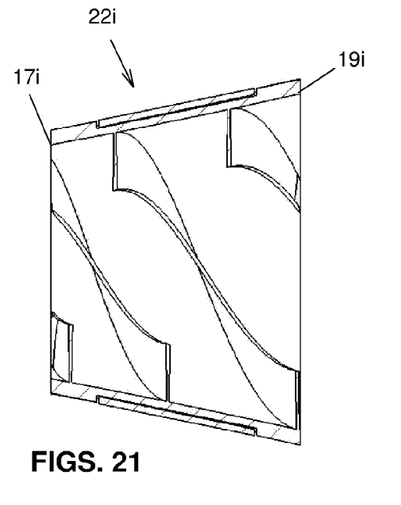
FIG. 21, in a side cross-sectional view, illustrates yet another alternative rotor usable in yet another alternative blood pump.

The housing 14 and rotor 22 both have a substantially cylindrical configuration. However, this is not necessarily the case in all embodiments of the invention. In alternative embodiments, the housing 14 and rotor 22 have any other suitable configuration. For example, as seen in FIG. 20, the rotor 22i tapers in a direction leading from the rotor outlet 19i to the rotor inlet 17i. In FIG. 21, the rotor 22j tapers in a direction leading from the rotor inlet 17j to the rotor outlet 19i. In FIGS. 20 and 21, rotors 22i and 22j both have a substantially frusto-conical configuration, and, typically, corresponding shaped housings (not shown in the drawings) are used.

Figures 10, 11, 12:
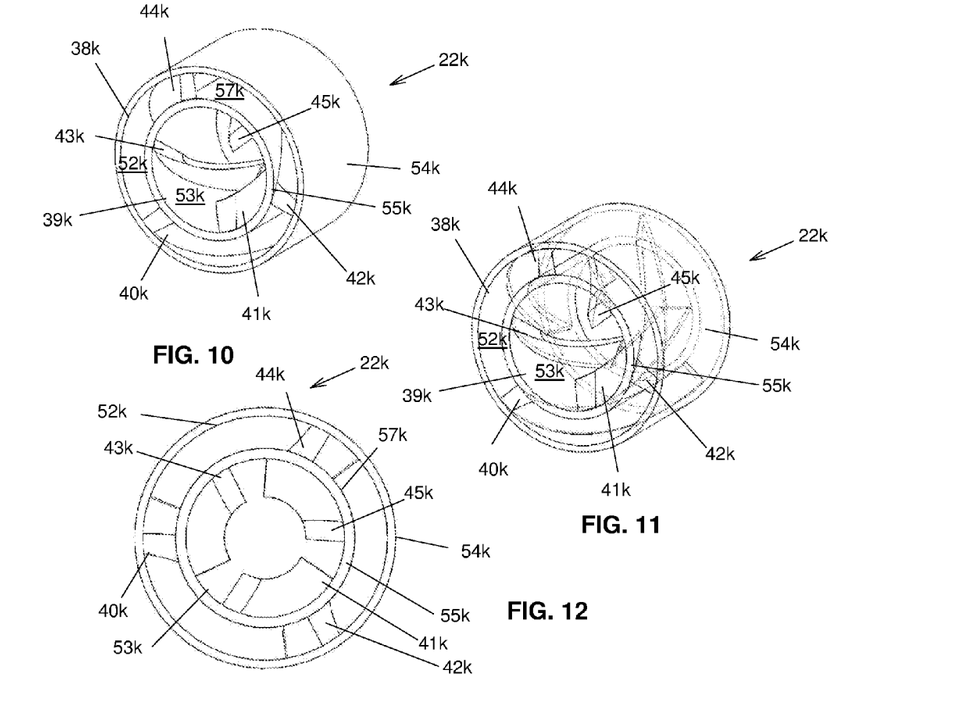

FIGS. 10 to 12 illustrate yet another rotor 22k usable instead of the rotor 22 in the pump 10. The rotor 22k includes a rotor body 54k at the periphery thereof delimiting a rotor passageway 38k extending axially therealong. The rotor body 54k defines a body internal surface 52k, which delimits the rotor passageway 38k.

An internal shroud 55k extends axially in the rotor passageway 38k, typically centred thereinto. For example, the internal shroud 55k is substantially cylindrical tubular and defines a shroud passageway 39k extending axially therealong. The internal shroud 55k defines a shroud external surface 57k facing the body internal surface 52k and a shroud internal surface 53k, which delimits the shroud passageway 39k.

The rotor 22k also includes rotor blades 40k, 41k, 42k, 43k, 44k and 45k. In alternative embodiments, there could be less than 6 or more than 6 rotor blades. At least one of the rotor blades 40k to 45k, for example rotor blade 40k, extends between the body internal surface 52k and the shroud external surface 57k. The rotor blade 40k thus does not have a free edge 62. The rotor blade 40k, and in the present embodiment the rotor blades 42k and 44k, support the internal shroud 55k in the rotor passageway 38k. At least one of the rotor blades, for example rotor blade 41k, extends from the shroud internal surface 53k, similarly in the way the rotor blades 40 to 44 extend from the rotor body 54. The rotor blades 40k and 41k have different configurations, for example different pitches. In some embodiments, the rotor blades 40k, 42k and 44k all have a first configuration and the rotor blades 41k, 43k and 45k all have a second configuration. However, other combinations for the configurations of the rotor blades 40k to 45k are within the scope of the invention, such as rotor blades 40k, 42k and 44k that between them have different configurations or rotor blades 41k, 43k and 45k that between them have different configurations. In some embodiments, as in the drawings, the rotor blades 40k, 42k and 44k are circumferentially offset relative to the rotor blades 41k, 43k, and 45k. However, other relative positions between the rotor blades 40k to 45k are within the scope of the invention.

All the rotor blades described in the present document may have a smooth surface, as shown, or alternatively a textured surface. Also, the rotor blades may be entirely contained in their respective rotor, or they may protrude axially therefrom, at one or both ends thereof.

Although the present invention has been described hereinabove by way of preferred embodiments thereof, it can be modified, without departing from the spirit and nature of the subject invention as defined in the appended claims.

What is claimed is:

1. An axial flow blood pump, comprising:
   a hollow housing defining a housing inlet, a housing outlet and a housing axial axis extending therebetween;
   a rotor mounted in the housing so as to be rotatable about the housing axial axis, the rotor including at least two rotor blades, a first rotor blade from the at least two rotor blades having a first configuration and a second rotor blade from the at least two rotor blades having a second configuration; and
   an actuator operatively coupled to the housing and to the rotor to selectively rotate the rotor in the housing about the housing axial axis;
   wherein the first and second configurations differ from each other;
   wherein the first and second rotor blades are coiled around the housing axial axis, the first rotor blade defining first blade inlet and outlet ends respectively receiving and releasing blood when the rotor is operated in a patient and the second rotor blade defining second blade inlet and outlet ends respectively receiving and releasing blood when the rotor is operated in a patient; and
   wherein the rotor is a hollow rotor including a rotor body at the periphery thereof delimiting a rotor passageway extending axially therealong, the rotor body defining a body internal surface delimiting the rotor passageway, the first and second blades extending from the body internal surface circumferentially spaced apart from each other.

2. The axial flow blood pump as defined in claim 1, wherein the first and second rotor blades each extend along a respective ruled surface.

3. The axial flow blood pump as defined in claim 1, wherein the first and second configurations differ in pitch relative to the housing axial axis.

4. The axial flow blood pump as defined in claim 3, wherein the pitch of the first blade is constant at all axial positions along the first blade.

5. The axial flow blood pump as defined in claim 1, wherein a third rotor blade from the at least two rotor blades has the first configuration and a fourth rotor blade from the at least two rotor blades has a second configuration, the third and fourth blades extending from the body internal surface.

6. The axial flow blood pump as defined in claim 5, wherein the second rotor blade is provided circumferentially between the first and third rotor blades.

7. The axial flow blood pump as defined in claim 1, wherein the first rotor blade defines a blade height at each given axial position therealong as a distance between the body internal surface and the radially inwardmost location of the first rotor blade at the given axial position, the first rotor blade having a substantially constant height axially therealong.

8. The axial flow blood pump as defined in claim 7, wherein the first and second rotor blades have different heights.

9. The axial flow blood pump as defined in claim 1, wherein the first rotor blade defines a blade height at each given axial position therealong as a distance between the body internal surface and the radially inwardmost location of the first rotor blade at the given axial position, the first rotor blade having a larger height at the first blade inlet end than at the first blade outlet end.

10. The axial flow blood pump as defined in claim 1, wherein the first rotor blade defines a blade height at each given axial position therealong as a distance between the body internal surface and the radially inwardmost location of the first rotor blade at the given axial position, the first rotor blade having a larger height at the first blade outlet end than at the first blade inlet end.

11. The axial flow blood pump as defined in claim 1, wherein the rotor defines an axially extending lumen unobstructed by the rotor blades, the lumen having a substantially constant transversal cross-sectional configuration axially therealong.

12. The axial flow blood pump as defined in claim 1, wherein the rotor defines an axially extending lumen unobstructed by the rotor blades, the lumen tapering in one of a direction leading from the first blade inlet end towards the first blade outlet end and a direction leading from the first blade outlet end towards the first blade inlet end.

13. The axial flow blood pump as defined in claim 1, wherein the first rotor blade increases in thickness in a direction leading from the first blade inlet end towards the first blade outlet end along at least part of the first rotor blade.

14. The axial flow blood pump as defined in claim 1, wherein the first rotor blade decreases in thickness in a direction leading from the first blade inlet end towards the first blade outlet end along at least part of the first rotor blade.

15. The axial flow blood pump as defined in claim 1, wherein the first rotor blade defines a first rotor blade inlet portion, a first rotor blade outlet portion and a gap therebetween.

16. The axial flow blood pump as defined in claim 1, wherein the first rotor blade is chamfered at the first blade inlet end.

17. The axial flow blood pump as defined in claim 1, further comprising at least one of
a flow inducer provided upstream of the housing inlet and including at least one vane which is shaped to redirect a blood flow entering the rotor to create a vortex; and
a diffuser provided downstream of the housing outlet and shaped for at least partial straightening of a blood flow exiting the rotor.

18. The axial flow blood pump as defined in claim 1, wherein the housing and rotor both have a substantially cylindrical configuration.

19. The axial flow blood pump as defined in claim 1, wherein the rotor defines axially opposed rotor inlet and outlet, the rotor tapering in a direction selected from a direction leading from the rotor inlet to the rotor outlet and a direction leading from the rotor outlet to the rotor inlet.

20. The axial flow blood pump as defined in claim 19, wherein the rotor has a substantially frusto-conical configuration.

21. The axial flow blood pump as defined in claim 1, wherein the first rotor blade extends circumferentially around the rotor over less than one full turn.

22. The axial flow blood pump as defined in claim 21, wherein the first rotor blade extends circumferentially around the rotor over one of less than half a full turn and less than a quarter of a full turn.

23. An axial flow blood pump, comprising:
a hollow housing defining a housing inlet, a housing outlet and a housing axial axis extending therebetween;
a rotor mounted in the housing so as to be rotatable about the housing axial axis, the rotor including at least two rotor blades, a first rotor blade from the at least two rotor blades having a first configuration and a second rotor blade from the at least two rotor blades having a second configuration; and
an actuator operatively coupled to the housing and to the rotor to selectively rotate the rotor in the housing about the housing axial axis;
wherein the first and second configurations differ from each other; and
wherein the rotor includes a rotor body at the periphery thereof delimiting a rotor passageway extending axially therealong, and an internal shroud extending axially in the rotor passageway, the rotor body defining a body internal surface, the internal shroud defining a shroud external surface facing the body internal surface and a shroud internal surface, the first rotor blade extending between the body internal surface and shroud external surface and the second rotor blade extending from the shroud internal surface.

24. An axial flow blood pump, comprising:
a hollow housing defining a housing inlet, a housing outlet and a housing axial axis extending therebetween;
a rotor mounted in the housing so as to be rotatable about the housing axial axis, the rotor including at least two rotor blades, a first rotor blade from the at least two rotor blades having a first configuration and a second rotor blade from the at least two rotor blades having a second configuration; and
an actuator operatively coupled to the housing and to the rotor to selectively rotate the rotor in the housing about the housing axial axis;
wherein the first and second configurations differ from each other;
wherein the first rotor blade either decreases or increases in thickness in a direction leading from the first blade inlet end towards the first blade outlet end along at least part of the first rotor blade.

* * * * *